United States Patent
Ralhan et al.

(10) Patent No.: US 6,730,514 B2
(45) Date of Patent: May 4, 2004

(54) STABLE HUMAN ORAL CANCER CELL CARCINOMA CELL LINE

(76) Inventors: Ranju Ralhan, S-16, Green Park (Main), New Delhi-110029 (IN); Jatinder Kaur, B-45 WZ/190 Srivaji Vimar Near Smivaji College, New Delhi-110027 (IN)

(*) Notice: Subject to any disclaimer, the term of this patent is extended or adjusted under 35 U.S.C. 154(b) by 0 days.

(21) Appl. No.: 09/730,567

(22) Filed: Dec. 7, 2000

(65) Prior Publication Data

US 2002/0110912 A1 Aug. 15, 2002

(51) Int. Cl.[7] ................................................ C12N 5/08
(52) U.S. Cl. ........................ 435/371; 435/325; 435/366
(58) Field of Search .............................. 435/325, 371, 435/366

(56) References Cited

PUBLICATIONS

Orkin, et al, Report and Recommendations of the Panel to Assess the NIH investment in Research on Gene Therapy, 1995.*
Marshall, Science, 1995, 269:1050–1055.*
Anderson, Nature, vol. 392, suppl. 1998, pp. 25–30.*
Verma, et al., Nature, vol. 389, 1997, pp. 239–242.*
Min et al., 1994, European J. of Cancer Part B: Oral Oncology 30/5 pp. 338–345.*
Kaur et al., 1998, Oral Oncology, 34(6) pp. 496–501.*
Braakhuis et al., 1997, British J. of Cancer 76(2) pp. 189–197.*

* cited by examiner

*Primary Examiner*—Mary E. Mosher
*Assistant Examiner*—Misook Yu
(74) *Attorney, Agent, or Firm*—Venable; Marina V. Schneller

(57) ABSTRACT

The present invention is directed to a stable, continuous, human oral squamous cell carcinoma cell line from the floor of the mouth of a habitual tobacco consumer using a variety of growth supplements and complement mediated lysis to obtain a fibroblast free culture. This cell line has the ability to produce tumor in athymic nude mice. The cell line of the present invention constitutes a system that is suitable for detecting and screening for new and effective anti-cancer therapies. This cell line provides in vitro and in vivo (xenographts in athymic mice) oral tumor model which is useful for understanding molecular basis of oral cancer development, identifying targets for designing novel therapeutic strategies, testing new gene therapy approaches for oral cancer and testing novel synthetic retinoids for chemoprevention of oral cancer.

1 Claim, No Drawings

STABLE HUMAN ORAL CANCER CELL CARCINOMA CELL LINE

BACKGROUND OF THE INVENTION

1. Field of the Invention

This invention relates to a stable human oral cancer cell carcinoma cell line suitable for understanding the differences in the tumorigenic pathways implicated in the development and progression of oral squamous cell carcinoma obtained from the floor of the mouth of a chronic tobacco consumer.

2. Background of the Related Art

Oral cancer ranks as the sixth most common globally and is a major cause of cancer-related morbidity and mortality. The aetiology of betel and tobacco related oral cancer is considerably different to that resulting from smoking of tobacco. Exposure of the oral mucosa of habitual betel quid chewers to a plethora of carcinogenic constituents of tobacco and areca nut causes multiple genotoxic insults at the site bolus application, often resulting in the development of clinically distinct premalignant lesions, leukoplakia or erthroplakia, which undergo malignant transformation. Established human oral cancer cell lines are widely used to study the mechanism implicated in oral tumorigenesis. The human oral cancer cell lines available in Cell Repositories and Culture Collections around the world have been established from the Western or Japanese population and resulting from smoking of tobacco. In this respect, reference is made to Table 1.

TABLE 1

REPORTED HEAD AND NECK SQUAMOUS CARCINOMA CELL LINES

| CELL LINE | Site | Study subject | Reference |
|---|---|---|---|
| SCC-40 | SP | Keratins | Wu et. al. 1982 |
| SqCC/Y1 | B | Retinoids; differentiation | Reiss, et. al. 1985 |
| HLC-1 | L | Cytogenetics | Hauser-Urfer et. al. |
| HTC-1 | T | | |
| HTC-2 | T | | |
| CAL-27 | T | Establishment: chemotherapy | Gioanni et. al. 1988 |
| CAL-33 | T | | |
| HN11 | FOM | Establishment: cytokiness | Meghji et. al. 1988 |
| HN12 | H | | |
| HN15 | FOM | | |
| HSC-2 | FOM | Establishment; metastasis | Momose et. al. 1989 |
| HSC-3 | T | | |
| HSC-4 | T | | |
| HST-1 | PE(T) | Establishment | Nakano et. al. 1989 |
| ZA | Ln(P) | Oncogenes | Todokoro et. al. 1989 |
| R105 | FOM | Establishment-differentiation | Crooijmans et. al. 1990 |
| T87/rc | E | | |
| SCC-83-01-82 | NS | Oncogenes-tumorigenicity | Shuler et. al. 1890 |
| Ca9-22 | G | | Rikimaru et. al. 1990 |
| H103 | T | Establishment | Prime et. al. 1990 |
| H157 | B | | |
| H314 | FOM | | |
| H191 | T | | |
| H140 | B | | |
| H357 | T | | |
| H376 | FOM | | |
| H400 | A | | |
| H413 | B | | |
| H440 | FOM | | |
| MH85 | M | Epidermal growth factor | Yoneda et. al. 1991 |
| UT-SCC-1A | G | Radiotheraphy | Pekkola et. al. 1991 |
| HOC605 | LN(P) | Epidermal growth factor | Rikimaru et. al. 1992 |
| HOC815 | LN(Mn) | | |
| HOC815 | LN(T) | | |
| HOC927 | LN(T) | | |
| T1/CUHK | T | Establishment | Chew et. al. 1992 |
| T2/CUHK | T | | |
| SCCKN | Oral | Establishment: chemotheraphy | Urade et. al. 1992 |
| SCCTF | Oral | | |
| EVSCC1 | A | p53 | Somers et. al. 1992 |
| EVSCC3 | T | | |
| EVSCC4 | FOM | | |
| JHU-011-SCC | R(L) | Interferons: integrins | Scher et. al. 1993 |
| JHU-220-SCC | L | | |
| JHU-022-SCC | Ln(L) | | |
| HNSCC28 | L | Radiobiology: cytogenetics | Cowan et. al. 1993 |
| HNSCC167 | To | | |
| HNSCC151 | T | | |
| HNSCC135 | HP | | |
| HNSCC294 | T | | |
| HNSCC143 | O | | |
| Tu-138 | G | Gene therapy, p53 | Liu et. al. 1994 |
| Tu-177 | L | | |
| H-1 | G | Establishment | Harada et. al. 1993 |
| KOSC-2 | FOM | Establishment: p53 | Inagaki et. al. 1994 |
| KOSC-3 | G | | |
| MISK81-5 | Ln(oral) | Establishment GCSF | Matsuo et. al. 1994 |
| FS-1 | M | Establishment: immunobiology | Fukiage et. al. 1994 |
| OSC-1 | T | Establishment-tumorigenicity | Osaki et. al. 1994 |
| OSC-2 | Ln(G) | | |
| OSC-3 | Ln(G) | | |
| OSC-4 | T | | |
| OSC-5 | T | | |
| OSC-6 | T | | |
| OSC-7 | T | | |
| MSK-922 | L | p53 expression | Xu et. al. 1994 |
| MSK-921 | T | | |
| MSK-QLL1 | T | | |
| MSK-QLL2 | L | | |
| MDA-686Ln | Ln(T) | | |
| MDA-686Tu | T | | |
| MDA-886Ln | Ln(L) | | |
| MDA-1186 | L | | |
| MDA-1386Ln | Ln(H) | | |
| MDA-1586 | L | | |
| MDA-1686 | B | | |
| MDA-1986 | Ln(T) | | |
| UT-SCC-1A | G | Radiosesitivity | Pekkolo-Heino et. al. 1994 |
| UT-SCC-1B | Met(G) | | |
| UT-SCC-2 | FOM | | |
| UT-SCC-4 | L | | |
| UT-SCC-5 | T | | |
| UT-SCC-6A | L | | |
| UT-SCC-6B | Met(L) | | |
| UT-SCC-8 | L | | |
| UT-SCC-9 | L | | |
| BICR3 | A | Tumor progression | Edington et. al. 1995 |
| BICR6 | H | | |
| BICR10 | B | | |
| BICR16 | R(T) | | |
| BICR18 | Met(L) | | |
| BICR22 | Met(T) | | |

TABLE 1-continued

REPORTED HEAD AND NECK
SQUAMOUS CARCINOMA CELL LINES

| CELL LINE | Site | Study subject | Reference |
|---|---|---|---|
| BICR31 | T | | |
| BICR56 | T | | |
| BICR63 | T | | |
| BICR68 | T | | |
| BICR78 | A | | |
| BICR82 | M | | |

A. alveolus; B. buccal mucosa; E. epiglottis; FOM. floor of mouth; G. gingiva, H. hypopharynx; HD. hard Palate; L. Larynx; M. maxilla; Mn. Mandible; O. oropharynx; P. palate; SP. soft palate; T. tongue; To. tonsil; LN 0. Lymph node metastasis (primary site); Met0. metastasis (primary site); PE0. Pleural effusion (primary Site); R0. recurrence (primary site); NS. not stated.

Presently, there are no oral cancer cell lines resulting from chewing of tobacco. Majority of the studies on oral carcinogenesis have been carried out using tissue specimens (biopsy or surgically resected oral premalignant and malignant lesions) or cell lines resulting from smoking of tobacco. Majority of the studies on oral carcinogenesis has been carried out using tissue specimens (biopsy or surgically resected oral premalignant and malignant lesions) or cell lines resulting from smoking of tobacco. The recent awareness of inherited nature of some cancers, ethnic groups, existence of cancer families and importance of surveillance of high risk individuals using cancer susceptibility genes as markers emphasizes the need to establish oral cancer cell lines resulting from chewing of tobacco to provide a much needed model for oral tumorigenesis. The existing oral cancer cell lines are from tobacco smokers and thus are not suitable for studies pertaining to cancer susceptibility originating from chewing of tobacco. It may be argued that these studies could be carried in human oral cancer tissue specimens. However, in-depth studies carried out by the applicants have shown that the availability of the tissue specimen poses a major constraint on the work. Often the biopsy/FNAC specimens yield insufficient number of tumor cells for detailed molecular analysis. Furthermore, the yield of RNA from biopsy/surgically resected tissue specimens may be low reducing the feasibility of conducting studies aimed at identification of genes that are differentially expressed in different stages of oral tumorigenesis by Differential Display Reverse Transcription Polymerase Chain Research (DDRT-PCR). Hence, the non-availability of an experimental model system for tobacco induced oral cancer is a major obstacle in understanding the mechanism underlying oral tumorigenesis. Establishment of human oral cancer cell lines from betel and tobacco consumers is of utmost importance to provide an in vitro experimental model system for oral tumorigenesis.

OBJECTS OF THE INVENTION

An object of this invention is to propose a human oral cancer line established and propogated in vitro from the oral squamous cell curcinome obtained from the floor of mouth of a chronic tobacco consumer.

Another object of this invention is to propose a human oral squamous cell carcinoma cell line from the floor of the mouth of a habitual tobacco consumer for the study of genetic/molecular alterations involved in development and progression of an environmental carcinogen induced malignancy.

Still another object of this invention is to propose a human oral cancer line established and propagated in vitro from the oral squamous cell curcinome obtained from the floor of mouth of a chronic tobacco consumer for indentifying novel targets for use as diagnostic/prognostic markers and designing new therapeutic strategies for more effective management of cancer patients.

Yet another object of this invention is to propose a human oral cancer line established and propogated in vitro from the oral squamous cell carcinoma obtained from the floor of mouth of a chronic tobacco consumer which may be advantageously used for various applications as described hereinbelow.

SUMMARY OF THE INVENTION

According to this invention there is provided human oral cancer cell line established and propagated in vitro from oral squamous cell carcinoma obtained from the mouth of a chronic tobacco consumer, wherein said cell line AMOS-III has the following marker profile:

a. positive for tumor suppressor gene product, p53; marker of invasion and metastasis, ets-1; ternary complex factors, Net and elk; retinoic acid receptors, RXR∝; RAR∝; anti-apoptotic protein and chaperone, HSP 70; epithelial specific antigen, ESA; human cytokeratin, CK 14, cell cycle regulatory protein, p21; Oncogene cyclin D1, heat shock protein, HSP90; transcription factor, ets-2; proliferation marker; Ki67.

b. Negative for human papilloma virus, HPV E6; mesenchymal cells marker, Vimentin; Low level of expression of oncogene MDM2, the p53 suppressor protein.

Further according to this invention there is provided a method of producing human oral cancer cell line which comprises:

a. subjecting oral squamous cell carcinoma from the floor of mouth to the step of biopsy in Hanks Balanced Salt Solution (HBSS) as a buffer supplemented with antibiotics (penicillin and streptomycin) and amphotericin B;

b. cutting the treated tissue of step (a) into smaller pieces;

c. washing the cut tissues with solution of antibiotics;

d. the washed tissues being introduced into tissue culture flasks having a medium comprising DMEM and Media 199 supplemented with fetal bovine serum (FBS) and growth supplements to allow the growth of cells comprising fibroblast cells which grow earlier than the epithelial cells.

e. Removing the fibroblasts cells from the culture to obtain a cell line comprising essentially of epithelial cells.

DESCRIPTION OF THE PREFERRED EMBODIMENTS

In accordance with this invention, tissue specimen was collected in the medium, DMEM supplemented with antibiotics (penicillin for example 100 U/ml and streptomycin for example 100 ug/ml). The specimens were washed several times with antibiotic solution before processing these for setting up the primary cultures. Tissue were minced into 1–2 cu.mm pieces using a cutting instrument, such as scalpel blade, and transferred into tissue culture flask containing DMEM supplemented with 10–20% FBS (fetal bovine serum), Glutamine for example 2 mM and growth factors such as epidermal growth factor (5–15 ng/ml). Initially, only limited success was achieved due to several inherent problems in obtaining contamination free oral tissue samples. The most perpetual problem encountered during the establishment of primary cultures/cell lines for oral SCC and leukoplakia was frequent bacterial and fungal contamination. Chronic exposure of the oral cavity to a variety of bacteria and viruses as well as to a plethora of known carcinogens viz., betel quid coated with lime, areca catechu, nut, alkaloids and tobacco often causes ulceration of the oral mucosa, thereby increasing the probability of contamination. Some of the other problems included, low yield of viable cells, poor adherence to the plastic substratum, slow growth, cell division and outgrowth of fibroblasts. To circumvent these problems several strategies were tried: a) patients were given thorough antibacterial and antifungal mouth wash several times prior to removal/resection of the tissue; subsequently tissue specimens were washed several times in DMEM containing solution of antibiotics (streptomycin, 100 ug/ml; pencillin 100 U/ml) and fungizone (0.25 ug/ml); b) tissue specimens were treated with different concentrations of collagenase or dispase to improve the yield of cells; c) Adherence of the cells was improved by testing several solid support systems such as precoating the tissue culture flask with varying concentrations of polylysine or collagen; d) to combat the problem of slow cell division various strategies were tried such as high FBS concentration, supplementation of growth medium with different growth factors such as Insulin, transferrin-selenium alone or in combination and epidermal growth factor (EGF, 10 ng/ml). Using several different permutations/ combinations and different concentrations of EGF, we could finally overcome these problems encountered during the process of establishment of primary cultures from oral SCCs.

One of the major problems faced in cultivation of epithelial cells is the out growth of fibroblasts. Fibroblasts grow more rapidly than epithelial cells and hence made culturing of epithelial cells quite difficult. Primary epithelial cultures that contained fibroblasts were treated with anti-fibroblast antibody, 1B10 that binds to the surface molecule of human. The cells were then treated with young rabbit serum (1:8 dilution in medium) as a source of complement. This lead to the complement mediated lysis of the fibroblast cells. Two to three such treatements gave a predominant population of epithelial cells, essentially free of fibroblasts. These cultures were allowed to grow to sub-confluency. Thereafter, the subconfluent cultures were subcultured and passaged at periodic intervals.

AMOS-III cultures were characterized including growth parameters, anchorage independent growth, morphological studies, immunological surface markers of epithelial lineage, karyotyping, DNA content and analysis of status of oncogenes, tumor suppressor genes and other cell cycle regulatory proteins and their expression.

The Cell Line can be used to i) investigate the basic/molecular machanisms and pathobiology of tabacco induced cancer of prime importance in the Indian context. The biological relevance of alterations in cell cycle regulatory genes such as p53, bcl-2, p21/waf1, mdm2 and HSP70.

ii) identify genes which are differentially expressed in oral cancer, iii) design novel gene therapy approaches for management or oral cancer.

iv) test the efficacy of novel synthetic retinoids for chemoprevention of oral cancer and indentify retinoid responsive genes, which are differentially expressed and provide insight into the mechanism of action of retinoids.

v) study mechanisms implicated in invasion and metastasis.

vi) understand the molecular mechanisms implicated in multidrug resistance, design novel multimodality therapeutic regimes for better management of the disease and design novel modulators for circumvention of drug resistance.

vii) The work assumes importance as supply of these cell lines to National and International Culture Collections would give an access of much needed in vitro experimental model system to several other laboratories/ regional centers which, due to limited resources, are unable to develop this facility on their own. In view of the aetiological and ethnic differences between the Indian and Western popoulation these cells lines are of considerable interest to the Western countries as well.

viii) Introduction of tumor suppressor genes eg. Transdominant (ligand inducible chimeric) tumor suppressor p53 constructs, or anti-sense approach against ix) oncogenes as shown for HSP70 in these cells is of tremendous value for designing new gene therapy approaches for oral cancer.

x) These cell lines can be used to study chromosomal aberrations occurring due to tobacco consumption.

TABLE 2

| Marker | Description | Reactivity | Method of analysis |
|---|---|---|---|
| p53 | tumor suppressor gene product | +++ | ICC |
| ets-1 | marker of invasion and metastasis | +++ | ICC |
| RXR∝ | retinoic acid receptor | ++ | ICC |
| RAR∝ | retinoic acid receptor | ++ | ICC |
| elk | ternary complex factor | ++ | ICC |
| Net | ternary complex factor | + | ICC |
| HSP70 | anti-apoptotic protein And chaperone | ++ | ICC |
| ESA | epithelial specific antigen | +++ | ICC |
| CK14 | human cytokeratin | +++ | ICC |
| p21 | cell cycle regulatory protein | ++ | ICC |
| cyclinD1 | Oncogene | ++ | ICC |
| HPV E6 | human papilloma virus | − | ICC |
| Vimentin | mesenchymal cell marker | − | ICC |
| MDM2 | oncogene, The p53 suppressor protein | + | ICC |
| HSP90 | Heat shak protein | ++ | ICC |
| Ets2 | transcription factor | ++ | ICC |
| Ki67 | proliferation marker | ++ | ICC |

Reactivity
− none
+ low
++ moderate
+++ high
Method of analysis
ICC immunocytochemistry

What is claimed is:

1. The human oral cancer cell line AMOS-III established and propagated in vitro from oral squamous cell carcinoma obtained from the mouth of a chronic tobacco chewer.

* * * * *